US006224603B1

(12) United States Patent
Marino

(10) Patent No.: US 6,224,603 B1
(45) Date of Patent: May 1, 2001

(54) TRANSILIAC APPROACH TO ENTERING A PATIENT'S INTERVERTEBRAL SPACE

(75) Inventor: James F. Marino, La Jolla, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 09/326,732

(22) Filed: Jun. 4, 1999

Related U.S. Application Data

(60) Provisional application No. 60/088,663, filed on Jun. 9, 1998, provisional application No. 60/120,663, filed on Feb. 12, 1999, and provisional application No. 60/129,703, filed on Apr. 16, 1999.

(51) Int. Cl.$^7$ ................................................. A61B 17/00
(52) U.S. Cl. ............................................................ 606/79
(58) Field of Search ............................. 606/79, 80, 171, 606/180

(56) References Cited

U.S. PATENT DOCUMENTS

| 3,128,768 | * | 4/1964 | Geistauts ........................ 128/305 |
| 4,696,308 | * | 9/1987 | Meller et al. .................... 128/754 |
| 4,756,309 | * | 7/1988 | Sachse et al. ................... 128/305 |
| 5,324,300 | * | 6/1994 | Elias et al. ....................... 606/180 |
| 5,330,488 | * | 7/1994 | Goldrath .......................... 606/148 |
| 5,484,437 | * | 1/1996 | Michelson ........................ 606/61 |
| 5,488,958 | * | 2/1996 | Topel et al. ...................... 606/180 |
| 5,591,187 | * | 1/1997 | Deckel ............................. 606/180 |
| 5,632,747 | * | 5/1997 | Scarborough et al. ........... 606/80 |
| 5,846,072 | * | 12/1998 | Furumoto et al. ................ 606/9 |
| 5,899,908 | * | 5/1999 | Kuslich et al. .................. 606/96 |
| 6,063,106 | * | 5/2000 | Gibson ............................. 606/232 |

FOREIGN PATENT DOCUMENTS

WO 99/16372    4/1999 (WO).

OTHER PUBLICATIONS

Osman, MD, Saidi G. et al., *Endoscopic Transiliac Approach to L5–S1 Disc and Foramen: A Cadaver Study,* Spine, 22, 11, pp. 1259–1263 (1997).

* cited by examiner

Primary Examiner—Gene Mancene
Assistant Examiner—Eduardo C. Robert
(74) Attorney, Agent, or Firm—Townsend and Townsend and Crew LLP

(57) ABSTRACT

The present invention provides methods for percutaneously accessing the patient's intervertebral space by creating an access portal through the patient's ilium and into the patient's intervertebral space. The access portal created by the present invention is preferably at a posterolateral angle, (preferably in the range of 40 to 90 degrees to an anterior-posterior axis through the patient), thereby being at the optimal angle of approach to the intervertebral space for these lower L5/S1 vertebrae. Methods are also provided for advancing surgical instruments through the passage and into the intervertebral space.

28 Claims, 10 Drawing Sheets

TRANSILIAC APPROACH TO ENTERING A PATIENT'S INTERVERTEBRAL SPACE

CROSS-REFERENCES TO RELATED APPLICATIONS

The present application is a regular application claiming benefit under 35 USC§119(e) from U.S. Provisional Patent Application Serial No. 60/088,663 filed Jun. 9, 1998; U.S. Provisional Patent Application Serial No. 60/120,663 filed Feb. 12, 1999; and Provisional U.S. Patent Application Serial No. 60/129,703 filed Apr. 16, 1999. Each of these applications is incorporated herein by reference in its entirety for all purposes.

BACKGROUND OF THE INVENTION

A major problem when accessing a patient's intervertebral space during spinal surgery is the problem of avoiding sensitive nerves and ligaments during the operative procedure. When accessing the para-spinal space or a specific intra-discal space to perform a discal or intervertebral procedure, the optimal angle of approach to avoid sensitive nerves and ligaments is a posterolateral angle. However, this angle of approach is not practical when accessing the lower vertebrae, specifically the L5/S1 inter-vertebral space, due to the patient's ilium bone which blocks such an angle of approach. Consequently, when performing surgical procedures at L5/S1 it is necessary to enter the intervertebral space from another angle, thus increasing the danger of interfering with the cauda equina and ligaments at such lower vertebrae.

SUMMARY OF THE INVENTION

The present invention provides methods for percutaneously accessing the patient's intervertebral space by creating an access portal through the patient's ilium and into the patient's intervertebral space. The access portal created by the present invention is preferably at a posterolateral angle, (preferably in the range of 40 to 90 degrees to an anterior-posterior axis through the patient), thereby being at the optimal angle of approach to the intervertebral space for these lower L5/S1 vertebrae. Methods are also provided for advancing surgical instruments through the passage and into the intervertebral space.

A system is also provided for conveying and depositing bone wax into bone interstices created by the coring of the ilium, thereby reducing bleeding.

As dual cannulae system of accessing a patient's intervertebral space is also provided.

DESCRIPTION OF THE SPECIFIC EMBODIMENTS

Figure 4:
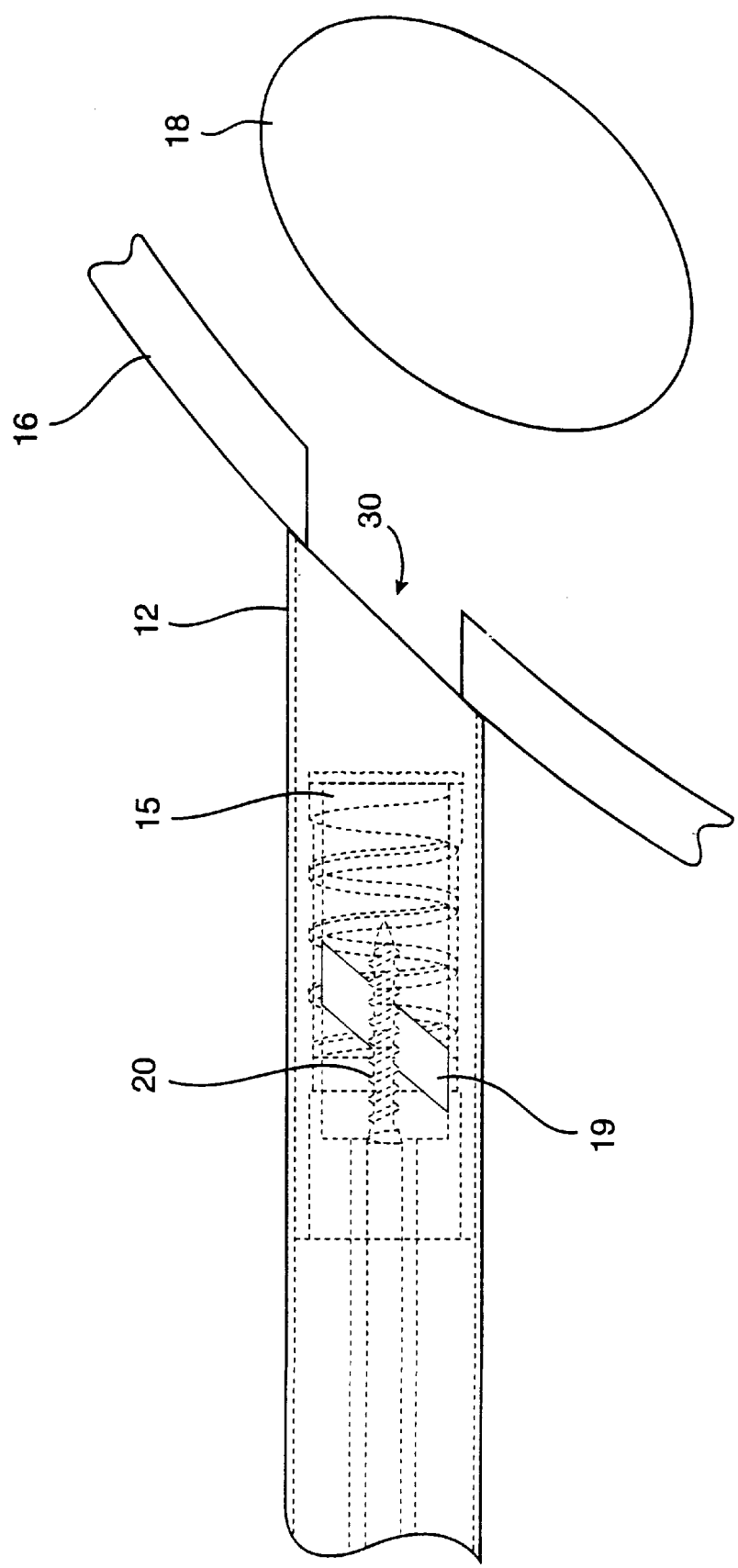
FIG. 4 is a schematic view of a cut-out section of the patient's ilium being removed by a cannulated fastening element.
Figure 5:
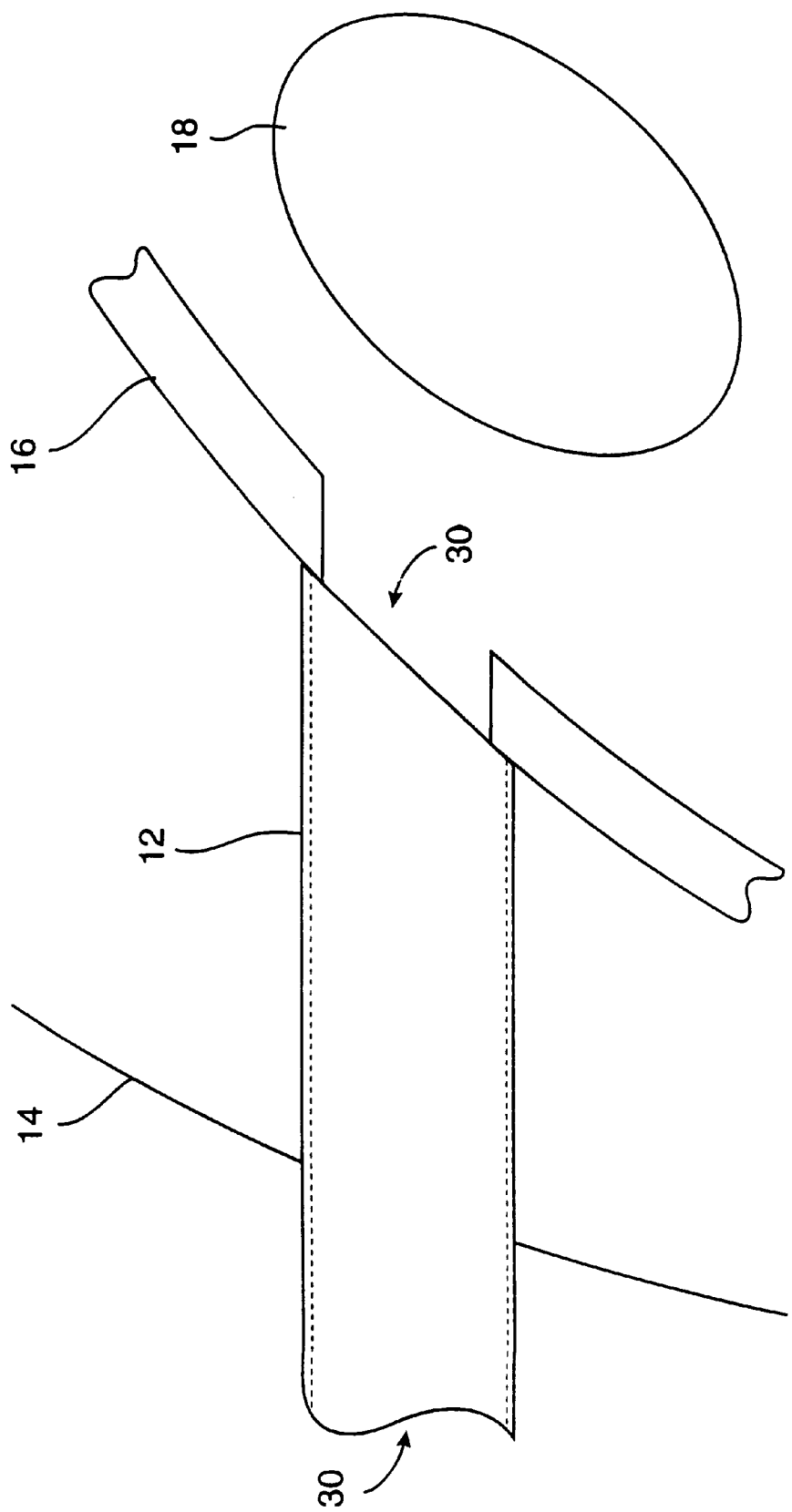
FIG. 5 is a schematic view of a cannulated access portal through the patient's ilium.
Figure 6:
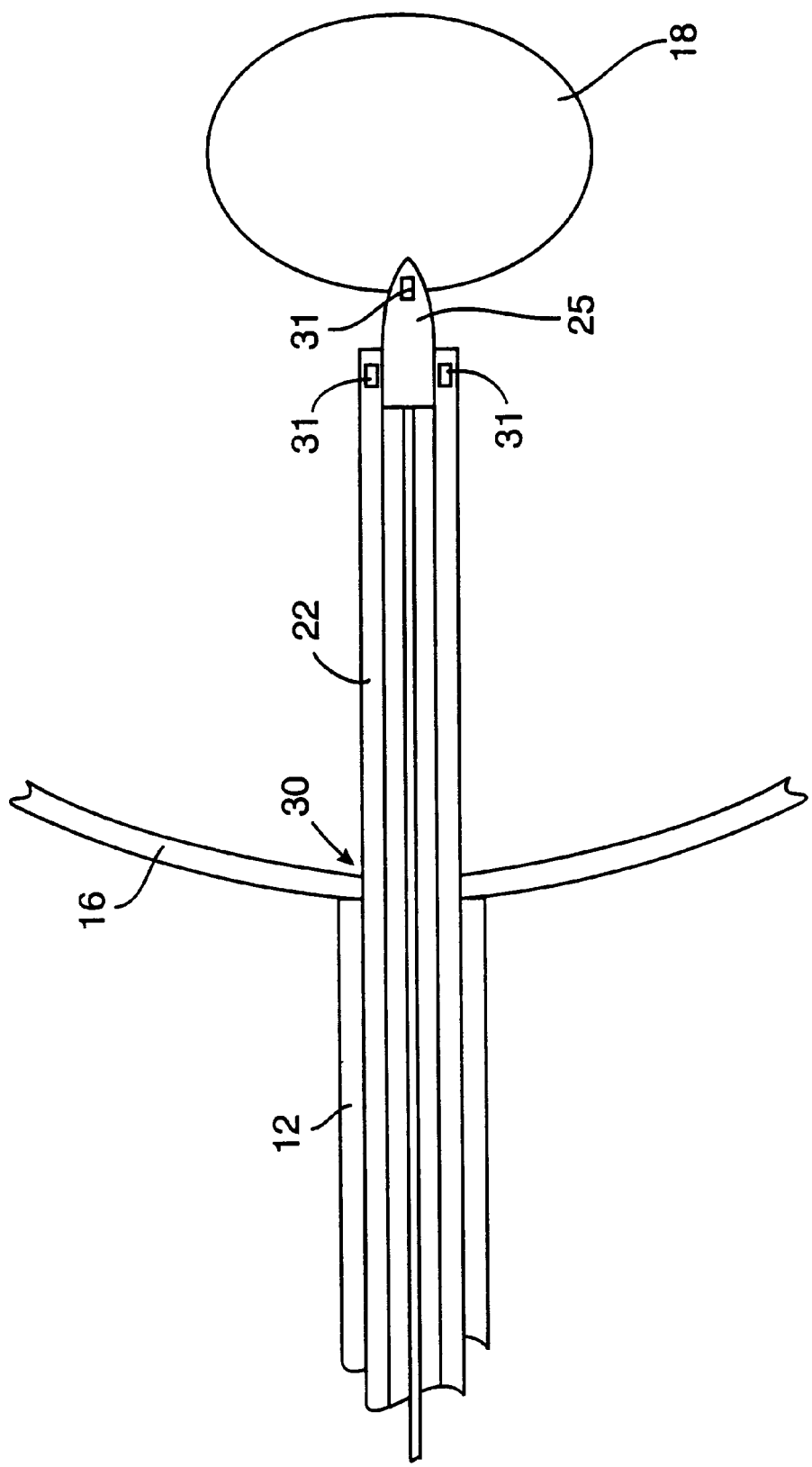
FIG. 6 is a schematic view of a surgical instrument passing through the patient's ilium and through a second cannula and into the patient's intervertebral space.

FIGS. 1–5 are to be viewed in sequence and show different aspects of the present method of providing a surgical access portal through a patient's ilium. FIG. 6 shows a method of inserting a surgical device into the intervertebral space through a second cannula which is received through the first cannula and through the access portal cut in the ilium.

Figure 1:
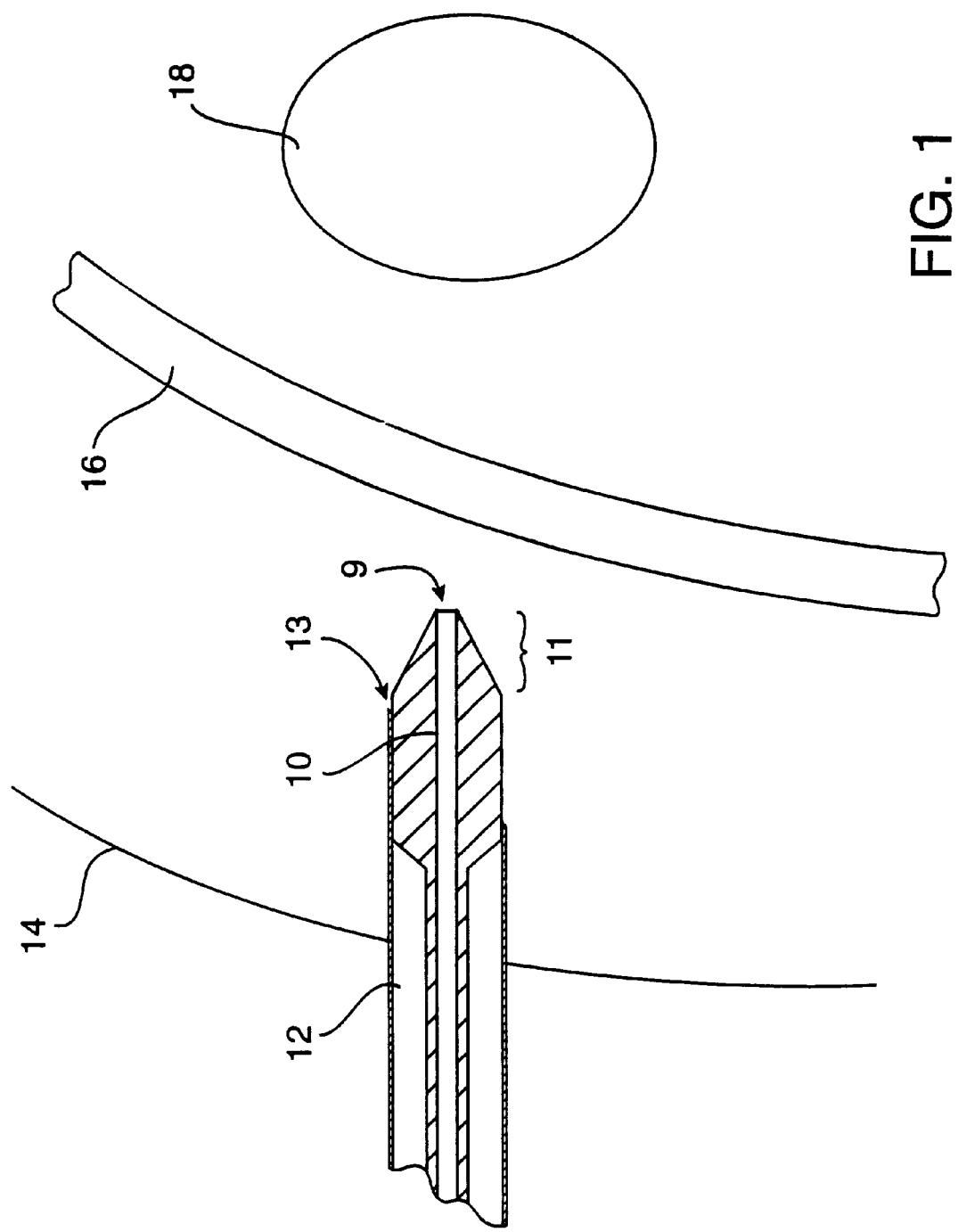
FIG. 1 is a schematic view of a cannulated obturator inserted percutaneously into the patient's back.
Figure 2:
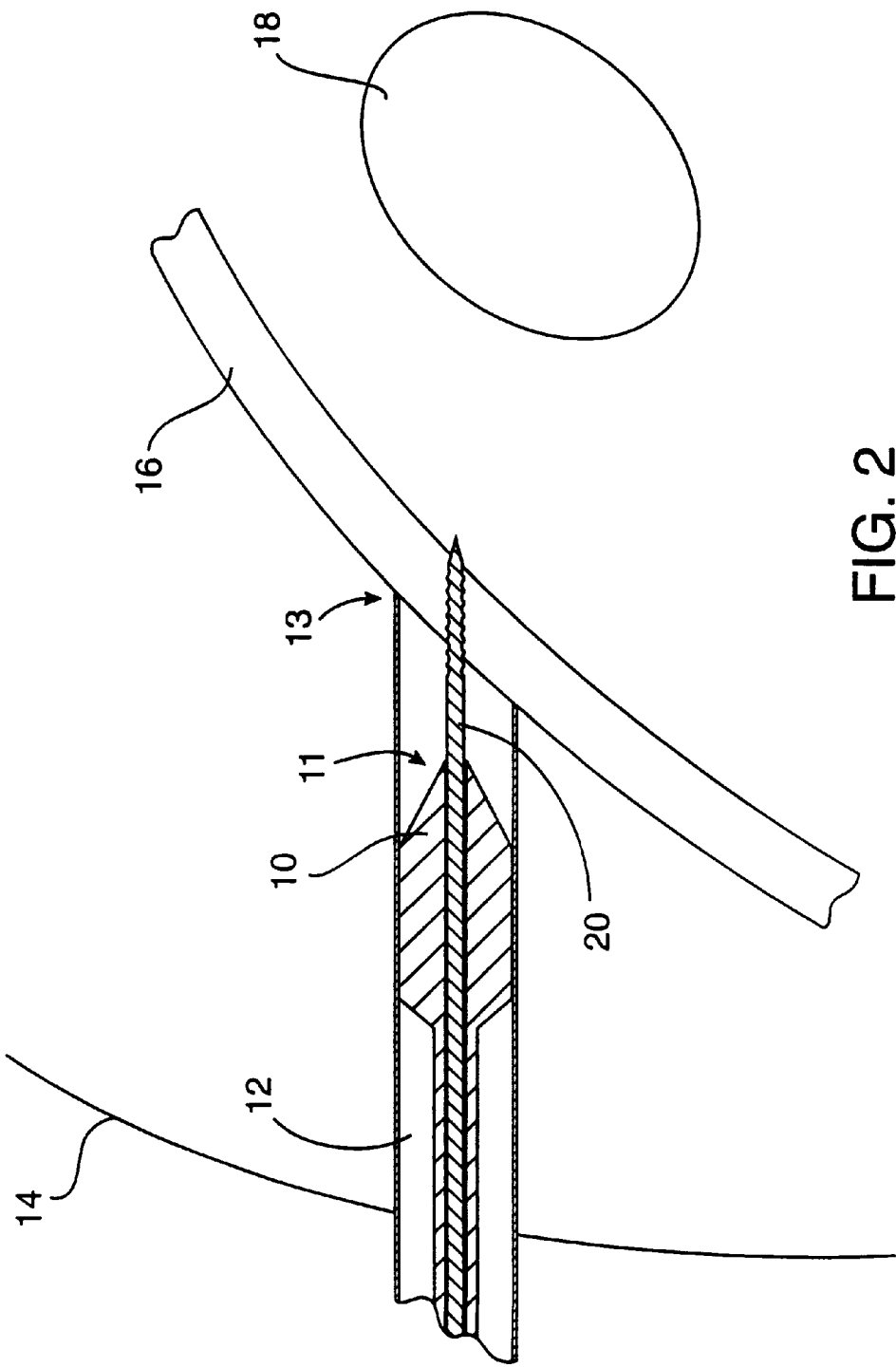
FIG. 2 is a schematic view of the cannulated obturator of FIG. 1 placed in contact with the patient's ilium, with a screw-fastening element inserted therethrough.

FIG. 1 shows a cannulated obturator 10 received in a cannula 12 which is percutaneously introduced through the back 14 of a patient having an ilium 16 and an intervertebral space 18. Obturator 10 has a narrow tapered end 11 enabling it to pass through the patient's tissues such that end 11 can be advanced to a position adjacent ilium 16 as is seen in FIG. 2. After obturator 10 reaches ilium 16, cannula 12 can be slipped down thereover such that a distal end 13 of cannula 12 can be placed in contact with ilium 16. Preferably, as is shown in FIGS. 1 and 2, distal end 13 of cannula 12 can have a angled end such that it can be rotated about its longitudinally extending central axis to abut against ilium 16 although ilium 16 is angled to cannula 12.

A fastening element is then attached to the ilium. In a preferred aspect, this fastening element comprises a screw-type fastening element 20 which is preferably held within bore 9 of obturator 10. Fastening element 20 can then be rotated to be screwed into ilium 16, as shown.

Figure 3A:
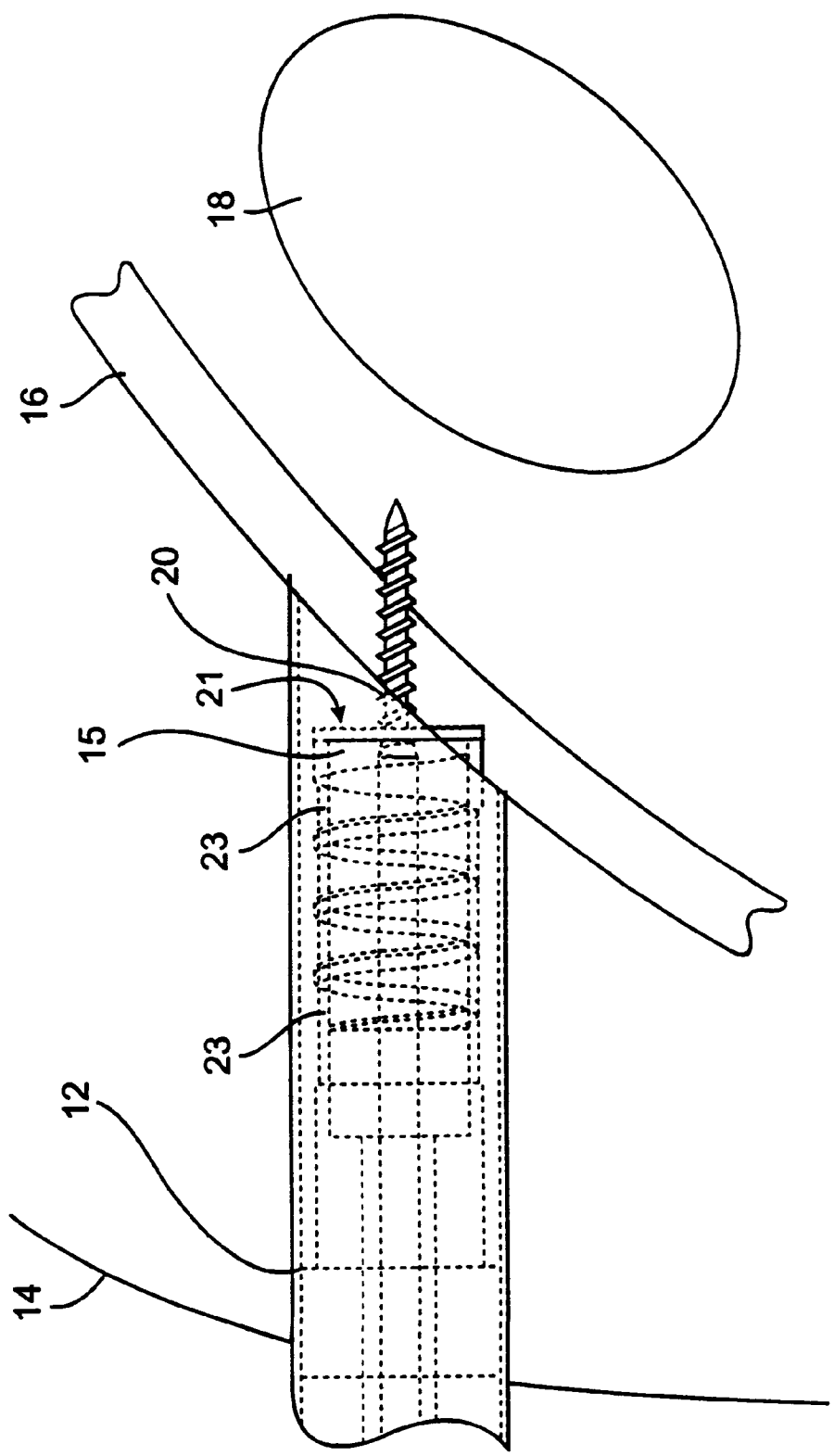
FIG. 3A is a schematic view of a bone cutting drill adapted with a spiral bonewax depression to deposit bone wax during cutting, with the fastening element screwed through the patient's ilium.
Figure 3B:
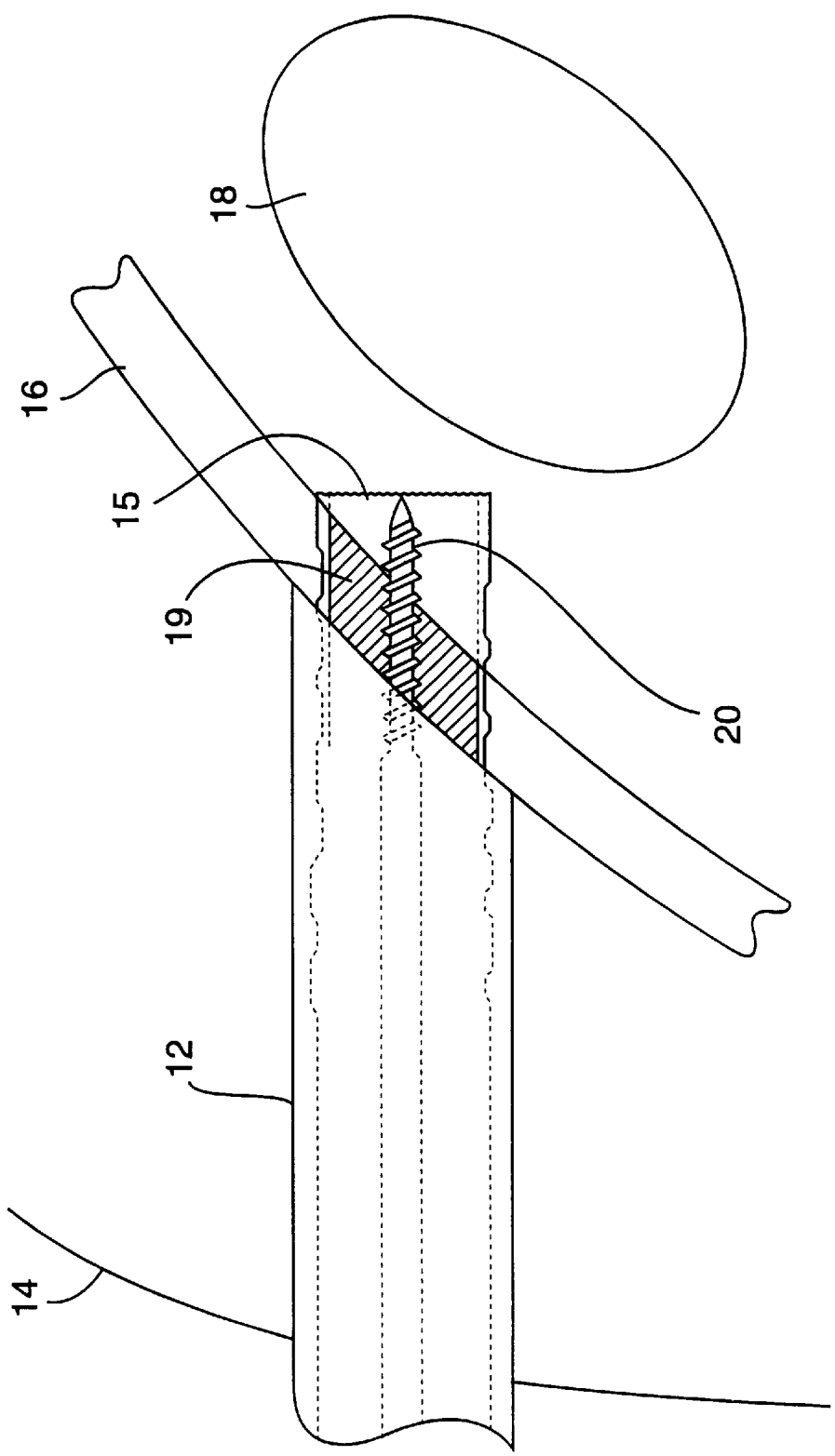
FIG. 3B shows the bone cutting drill advanced through the patient's ilium.

As seen in FIG. 3A, obturator 10 is then removed and a bone cutting device 15, which is preferably hollow as shown, is inserted into cannula 12 over fastening screw 20 such that bone cutting device 15 abuts against ilium 16. Screw-type fastening element 20 is received within a hollow bore 21 of bone cutter 15 as shown. Back and forth oscillation or continuous rotation of bone cutter 15 will eventually bore through ilium 16 to the position shown in FIG. 3B.

Bone cutter 15 is adapted to provide for the conveyance and deposition of bone wax into bone interstices created by the coring of the ilium, thereby reducing intraoperative and postoperative bleeding. Specifically, spiral grooves 23 on the exterior surface of bone cutter 15 are adapted to hold bone wax or paraffin therein such that the bone wax or paraffin will be heated and melt with the cutting friction, thereby being deposited into the cored bone region. Accordingly, bone healing is promoted.

In a preferred aspect, bone cutter 15 comprises an oscillating "cast" drill (ie: a drill which cuts through rigid objects but not soft objects), which is adapted to cut through the hard bony tissue of the ilium without damaging softer surrounding tissues.

As shown in FIG. 4, oscillation or rotation of bone cutter 15 will eventually cut out a circular section 19 of ilium 16 which can be removed as follows. Since fastening element 20 is rotated to be screwed into section 19 of ilium 16, removal of fastening element 20 and bone cutter 15 from within cannula 20 will thus also cause circular cut-out section 19, (which is attached to fastening element 20), to be removed as well. When bone cutter 15 and fastening element 20 are simultaneously removed, section 19 will preferably remain within the cannula of bone cutter 15. Rotational or axial movement of fastening element 20 relative to bone cutter 15 will subsequently remove section 19 from the cannula of bone cutter 15. As a result, a cannulated access portal 30 will be provided passing percutaneously through the patient's ilium as is shown in FIG. 5.

Subsequently, as is shown in FIG. 6, a surgical tool 25 which may comprise an intervertebral insert, bone decorticator, camera, articulating forceps, intervertebral insert positioning systems, bone-graft introducer, electrocoagulator, bone wax applicator, shaver or curette, can then be inserted through cannula 20 and through ilium 16 such that surgical tool 25 can reach intervertebral space 18. Specifically, in a preferred aspect, a second cannula 22 is dimensioned to be slidably received within first cannula 12 such that cannula 22 can be advanced to intervertebral space 18. Surgical tool 25 can then be inserted therethrough such that surgical tool 25 can be positioned at intervertebral space 18, as shown. In a preferred aspect, the second cannula may have an oval cross section.

In another preferred aspect, nerve surveillance electrodes 31 are positioned at the distal end of cannula 22 or on surgical device 25, (which may comprise a blunt obturator). Electrodes 31 can be adapted to sense the presence of a para-spinal nerve as cannula 22 is advanced through access portal 30. In alternative aspects, expandable trocars may be inserted through cannula 22 to access the patient's intervertebral space.

Cut-out section 19 can itself be used as bone graft material for packing around or within intervertebral inserts which are positioned in the intervertebral space using the present system.

Figure 9:
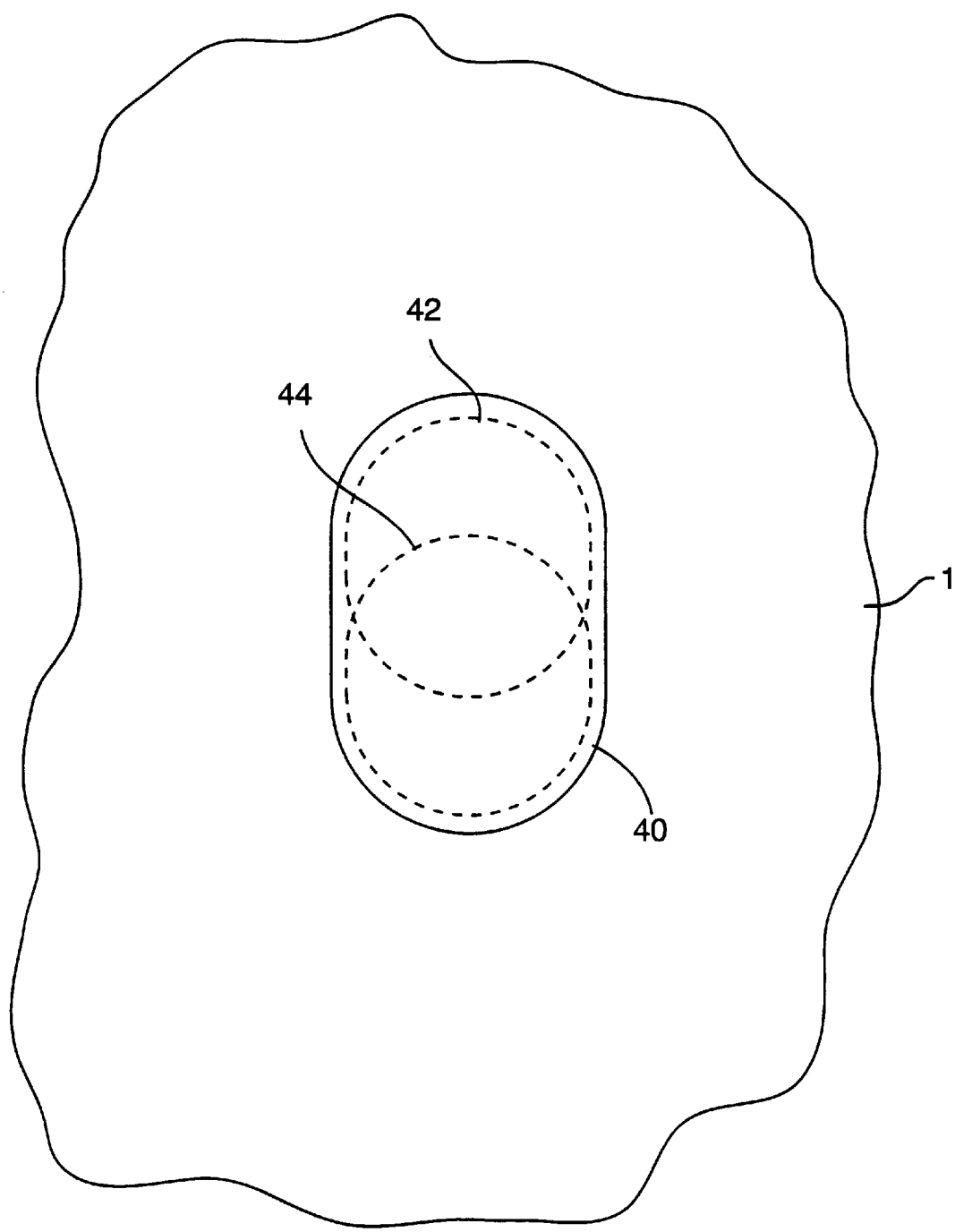
FIG. 9 is a view of a racetrack-shaped hole passing through the ilium.

As is shown in FIG. 9, a racetrack-shaped hole 40 can be drilled through the ilium 16 by sequentially drilling overlapping first and second circular holes 42 and 44 using the present method. As can be appreciated holes of various shapes, (including elongated racetrack shapes), can be drilled through the patient's ilium. An advantage of racetrack-shaped hole 40 is that it permits cannulae having oval or racetrack-shaped cross sections to be passed through ilium 16, and into the patient's intervertebral region.

As the present invention is adapted to provide a passage through the patient's ilium as is set forth herein, an optimal posterolaterally angled access portal through to the patient's L5/S1 intervertebral spaces can be provided.

Figure 7:
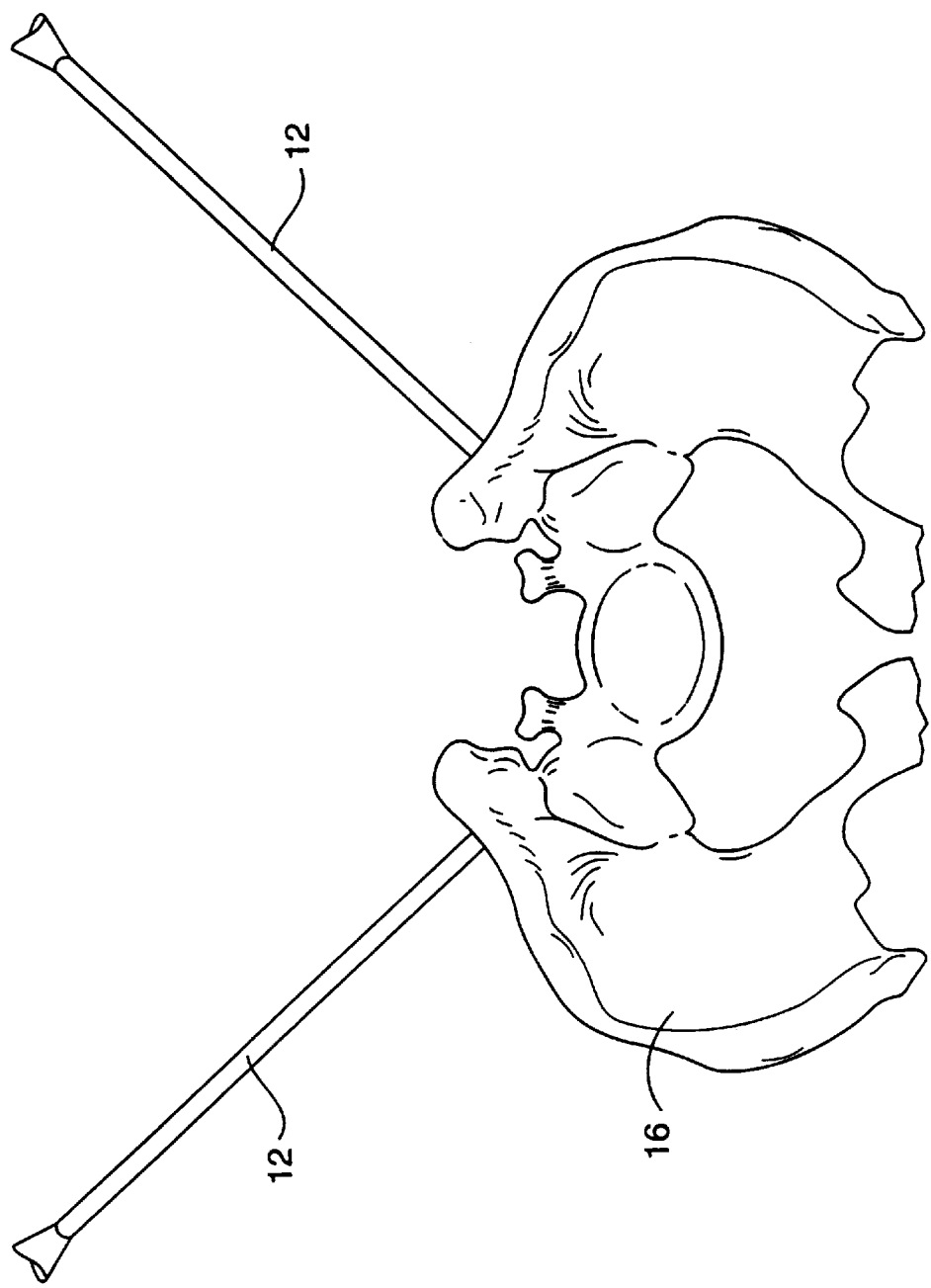
FIG. 7 is an illustration of a pair of percutaneously inserted cannulae approaching a patient's ilium in postero-lateral angles.
Figure 8:
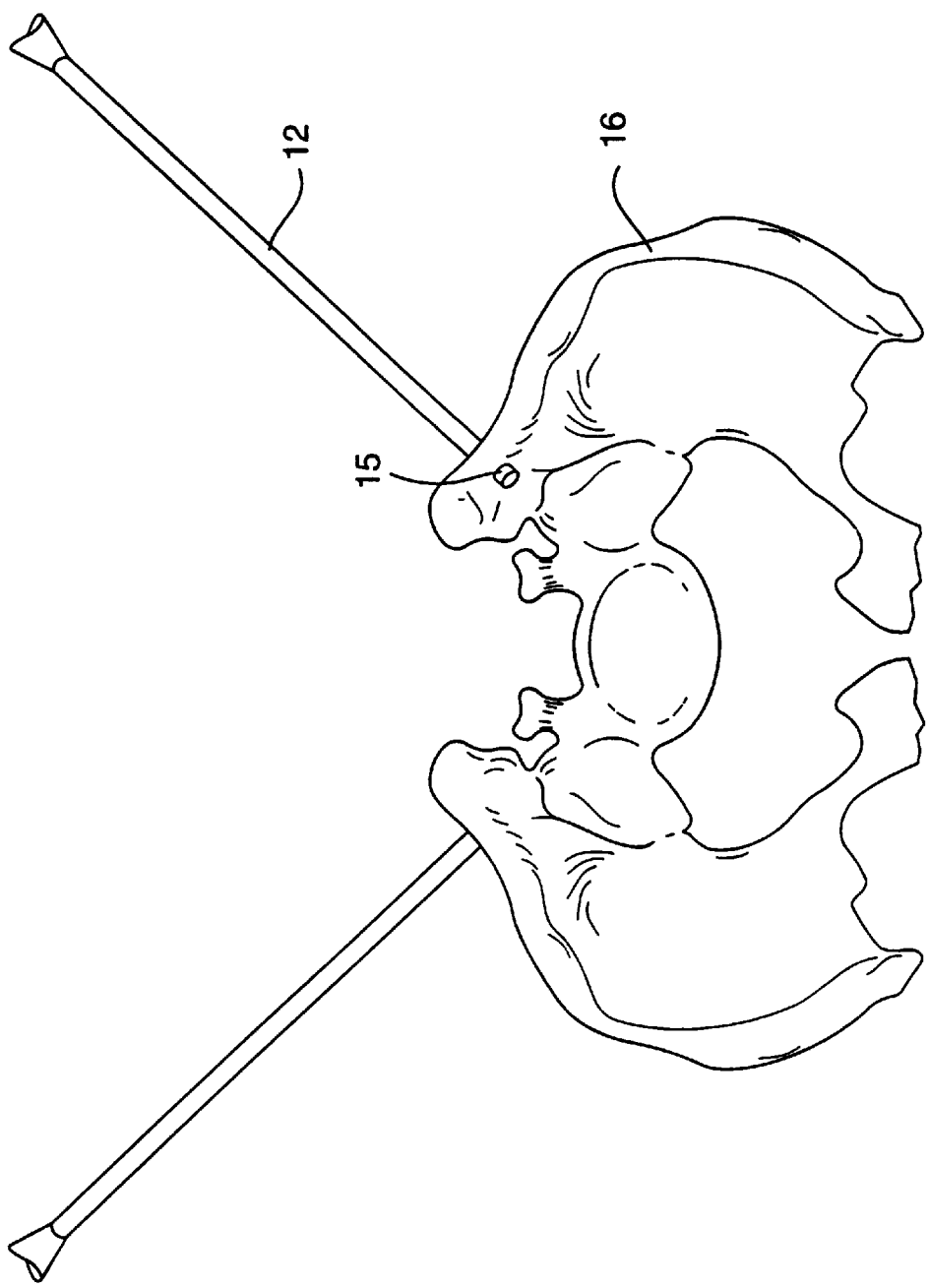
FIG. 8 is an illustration of a pair of percutaneously inserted cannulae approaching a patient's ilium in postero-lateral angles with a bone cutter passing through the patient's ilium.

FIG. 7 shows a pair of percutaneously inserted cannulae 12 approaching the patient's ilium 16 in posterolateral angles, which are preferably in the range of 40° to 90° to an anterior axis through the patient. FIG. 8 shows the pair of percutaneously inserted cannulae 12 positioned against the patient's ilium 16 in posterolateral angles with the distal end of bone cutter 15 passing through patient's ilium 16.

The present invention also provides kits for providing a surgical access portal through a patient's ilium, comprising: a cannula; a bone cutting drill dimensioned to be received within the cannula; a fastening element dimensioned to be received within the bone cutting drill; and instructions for use setting forth any of the methods herein described.

The present invention also provides kits for providing access to a patient's intervertebral space through a patient's ilium, comprising: a first cannula; a bone cutting drill dimensioned to be received within the first cannula; a fastening element dimensioned to be received within the bone cutting drill; and instructions for use setting forth any of the methods herein described.

What is claimed is:

1. A method of providing a surgical access portal through a patient's ilium, comprising:

positioning a distal end of a cannulated obturator against the patient's ilium;

advancing a fastening element through the cannula of the obturator so that the fastening element reaches the patient's ilium;

securing the fastening element to the patient's ilium;

advancing a cannulated bone cutting drill over the of a fastening element such that a distal end of the e cannulated bone cutting drill contacts the patient's ilium;

drilling a hole through the patient's ilium with the bone cutting drill;

removing a circular cut portion of the ilium attached to the fastening element, thereby providing an access portal through the patient's ilium.

2. The method of claim 1, further comprising:

introducing the cannulated obturator in to the patient through a percutaneously inserted first cannula.

3. The method of claim 2, wherein the first cannula is introduced in a posterolateral approach.

4. The method of claim 3, wherein, the posterolateral approach is at an angle of in the range of 40 to 90 degrees to an anterior-posterior axis through the patient.

5. The method of claim 1, further comprising accessing a patient's intervertebral space by:

inserting a second cannula through the first cannula; and advancing a distal end of the second cannula through the access portal in the ilium and into the patient's intervertebral space.

6. The method of claim 5, further comprising:

advancing a surgical instrument through the access portal and into the intervertebral space.

7. The method of claim 6, wherein advancing a surgical instrument comprises advancing an intervertebral insert, bone decorticator, camera, articulating forceps, intervertebral insert positioning systems, bone-graft introducer, electrocoagulator, bone wax applicator, shaver or curette into the intervertebral space.

8. The method of claim 1, wherein, the first cannula has a longitudinal axis extending therethrough and the distal end of the first cannula is angled with respect to the longitudinal axis, wherein positioning the distal end of the first cannula comprises rotating the first cannula about the longitudinal axis such that the angled end substantially fully contacts the ilium.

9. The method of claim 1, wherein, securing the fastening element to the ilium comprises screw-fastening a distal end of the fastening element into the ilium.

10. The method of claim 1, wherein, the bone cutting drill and the fastening element are removed simultaneously from the first cannula with the circular cut portion of the ilium held within the bone cutting drill.

11. The method of claim 10, wherein, the circular cut portion of the ilium is removed from the bone cutting drill by displacing an axially-adjustable plug in the bone cutting drill.

12. The method of claim 11, wherein, the axially-adjustable plug is received over the fastening element and within the bone cutting drill.

13. The method of claim 1, further comprising,
depositing bone wax around the surface of the hole as the hole is drilled through the ilium.

14. A kit for providing a surgical access portal through a patient's ilium, comprising:
   a cannula;
   a bone cutting drill dimensioned to be received within the cannula;
   a fastening element dimensioned to be received within the bone cutting drill; and
   means for instructing an user to provide a surgical access portal through the patient's ilium as set forth in method claim 1.

15. A system for providing a surgical access portal through a patient's ilium, comprising:
   a first cannula;
   a hollow bone cutting drill dimensioned to be received within the first cannula, the bone cutting drill dimensioned to receive cut away bone material therein, and having a grooved exterior surface holding bone wax or paraffin therein; and
   a fastening element dimensioned to be received within the hollow bone cutting drill.

16. The system of claim 15, wherein, the first cannula has an annular cross-section.

17. The system of claim 15, wherein, the bone cutting drill is an oscillating drill.

18. The system of claim 15, wherein, the fastening element has a distal end shaped to be screw-fit into the ilium.

19. The system of claim 15, wherein, the first cannula has an angled distal end.

20. The system of claim 15, wherein, the first cannula has a round or oval-shaped cross section.

21. The system of claim 15, further comprising, a second cannula dimensioned to be received within the first cannula.

22. The system of claim 21, wherein, the second cannula has a round or oval-shaped cross section.

23. The system of claim 22, further comprising, an expandable trocar dimensioned to be received within the first and second cannulae.

24. The system of claim 21, further comprising, a surgical instrument dimensioned to be received within the second cannula.

25. The system of claim 24, wherein, the surgical instrument is an intervertebral insert, bone decorticator, endoscope, articulating forceps, intervertebral insert positioning systems, bone-graft introducer, electrocoagulator, bone wax applicator, shaver or curette.

26. The system of claim 21, further comprising, an intervertebral implant dimensioned to be received within the first and second cannulae.

27. The system of claim 21, wherein the second cannula has at least one nerve surveillance electrode disposed at a distal end.

28. A system for providing a surgical access portal through a patient's ilium, comprising:
   a first cannula;
      a bone cutting drill dimensioned to be received within the first cannula;
   a fastening element dimensioned to be received within the bone cutting drill;
   a second cannula dimensioned to be received within the first cannula wherein the second cannula has a round or oval-shaped cross section; and
   an expandable trocar dimensioned to be received within the first and second cannulae.

* * * * *